US012611327B2

(12) United States Patent
Doppelstein et al.

(10) Patent No.:  US 12,611,327 B2
(45) Date of Patent:      Apr. 28, 2026

(54) MULTI-IMPLEMENT SURGICAL DEVICE

(71) Applicant: Alcon Inc., Fribourg (CH)

(72) Inventors: Alexander Doppelstein, Spaichingen (CH); Reto Grüebler, Greifensee (CH)

(73) Assignee: Alcon Inc., Fribourg (CH)

( * ) Notice: Subject to any disclaimer, the term of this patent is extended or adjusted under 35 U.S.C. 154(b) by 480 days.

(21) Appl. No.: 18/059,592

(22) Filed: Nov. 29, 2022

(65) Prior Publication Data

US 2023/0172750 A1      Jun. 8, 2023

Related U.S. Application Data

(60) Provisional application No. 63/265,071, filed on Dec. 7, 2021.

(51) Int. Cl.
    *A61F 9/007*      (2006.01)
    *A61B 90/30*      (2016.01)

(52) U.S. Cl.
    CPC .............. *A61F 9/007* (2013.01); *A61B 90/30* (2016.02)

(58) Field of Classification Search
    CPC ...... A61F 9/007; A61F 9/00736; A61B 90/30; A61B 90/92; A61B 2017/00349; A61B 2017/00353; A61B 2017/00362; A61B 2017/22074; A61B 2090/306; A61B 17/30; A61B 2017/305; A61B 2017/320008
    See application file for complete search history.

(56) References Cited

U.S. PATENT DOCUMENTS

| | | | |
|---|---|---|---|
| 2,468,258 A | | 4/1949 | Fahringer et al. |
| 2,781,741 A | | 2/1957 | Paul |
| 3,260,242 A | | 7/1966 | Liguori |
| 5,456,695 A | * | 10/1995 | Herve Dallemagne ...................... A61B 17/0218 606/198 |
| 5,743,582 A | | 4/1998 | Rivera |
| 7,020,922 B2 | | 4/2006 | Rivera |
| 10,500,090 B2 | | 12/2019 | Gunn et al. |
| 10,667,685 B2 | | 6/2020 | Chang et al. |
| 11,433,174 B2 | | 9/2022 | Grueebler et al. |
| 2004/0068253 A1 | * | 4/2004 | Bayer ................ A61B 17/3211 606/1 |
| 2004/0249366 A1 | * | 12/2004 | Kunz ............... A61B 17/00234 606/1 |
| 2007/0191823 A1 | | 8/2007 | Scheller |
| 2008/0195135 A1 | | 8/2008 | Attinger |

(Continued)

FOREIGN PATENT DOCUMENTS

| | | |
|---|---|---|
| WO | 2014200737 A1 | 12/2014 |
| WO | 2016064580 A1 | 4/2016 |
| WO | 2021220109 A1 | 11/2021 |

*Primary Examiner* — Benjamin J Klein
*Assistant Examiner* — Alisha J Sircar
(74) *Attorney, Agent, or Firm* — PATTERSON + SHERIDAN, LLP

(57) ABSTRACT

A device for surgery that accommodates multiple different implements. The implements may be exchanged or changed out for one another over the course of a surgery in a manner that does not require disengagement of the device from a surgical site. As a result, the need to re-insert the device into the patient and other hazards associated with multiple trips into the surgical site may be minimized. In one embodiment, the device includes cannula architecture to avoid use of a separate cannula at the surgical site.

8 Claims, 6 Drawing Sheets

(56)  References Cited

U.S. PATENT DOCUMENTS

| 2009/0163943 | A1* | 6/2009 | Cavanaugh | ............ | A61B 17/30 |
| | | | | | 606/180 |
| 2009/0287143 | A1 | 11/2009 | Line | | |
| 2010/0063437 | A1* | 3/2010 | Nelson | ............... | A61B 17/3439 |
| | | | | | 606/1 |
| 2014/0023423 | A1* | 1/2014 | Branch | ................. | B43K 24/12 |
| | | | | | 401/23 |
| 2014/0074116 | A1* | 3/2014 | Collins | ................. | A61B 90/92 |
| | | | | | 606/130 |
| 2015/0335378 | A1* | 11/2015 | Kleih | ................. | A61B 18/1482 |
| | | | | | 606/41 |
| 2017/0165114 | A1* | 6/2017 | Hallen | ................. | A61F 9/00736 |
| 2018/0042772 | A1* | 2/2018 | Mansour | ............ | A61F 9/00736 |
| 2018/0221562 | A1* | 8/2018 | Gomez | ............ | A61B 18/1482 |
| 2020/0178948 | A1* | 6/2020 | Piskun | ............... | A61B 1/00135 |
| 2020/0397476 | A1 | 12/2020 | Schaller | | |
| 2020/0397477 | A1* | 12/2020 | Schaller | ................. | A61F 9/007 |
| 2021/0128195 | A1 | 5/2021 | Abt | | |
| 2022/0125284 | A1 | 4/2022 | Hallen | | |
| 2022/0193311 | A1 | 6/2022 | Gruebler et al. | | |

* cited by examiner

MULTI-IMPLEMENT SURGICAL DEVICE

CROSS-REFERENCE TO RELATED APPLICATIONS

This application claims the benefit of priority of U.S. Provisional Patent Application Ser. No. 63/265,071 titled "MULTI-IMPLEMENT SURGICAL DEVICE," filed on Dec. 7, 2021, which is hereby incorporated by reference in its entirety as though fully and completely set forth herein.

BACKGROUND

Over the years, many dramatic advancements in the field of minimally invasive surgical procedures have taken place. Accordingly, natural patient injury and healing times have been dramatically reduced. In the area of eye surgery as an example, previously inaccessible injured or deteriorating tissue may now be repaired or directly serviced through minimally invasive procedures. For example, vitrectomy is the removal of some or all of the vitreous humor from a patient's eye. In some cases, where the surgery was limited to removal of clouded vitreous humor, the vitrectomy may constitute the majority of the procedure. However, a vitrectomy may accompany cataract surgery, surgery to repair a retina, to address a macular pucker or a host of other issues.

In keeping with the example of eye surgery and a vitrectomy, the vitreous humor itself is a clear gel that may be removed by an elongated needle when inserted through a pre-placed cannula at the eye. More specifically, a vitrectomy probe is a surgical tool that is held by a surgeon at a gripping location with a needle emerging from the tool as described. The needle includes a central channel for removal of the vitreous humor. Further, the cannula provides a structurally supportive conduit strategically located at an offset location at the front of the eye, such as the pars plana. In this way, the probe needle may be guidingly inserted into the eye in a manner that avoids damage to the patient's lens or cornea.

The needle is generally guided and supported by a cannula and trocar assembly which has been prepositioned at the location of an incision through the pars plana as indicated. Thus, the needle may be securely advanced through to the interior of the eye to perform the surgical procedure. Of course, just as with a probe needle for a vitrectomy, a variety of other surgical implements may be similarly advanced through a cannula and trocar assembly for a variety of different surgical purposes. These may include forceps, scissors, light and other instrumentation.

Over the course of a given surgery, it is generally the case that more than one different type of manipulative instrument may be called for. For example, while a light instrument may be positioned to support the surgery and left in place, a more actively interventional or "manipulative" instrument such as the vitrectomy probe may be used, removed and replaced with another. Consider the example of a vitrectomy that takes place for a period followed by the use of forceps or scissors to address a hemorrhage or other issue that is not adequately dealt with by the vitrectomy probe. This would include multiple different trips into the eye with a fairly sharp probe or needle. For example, a vitrectomy probe might be inserted and removed from the eye, followed by the separate insertion and withdrawal of the indicated forceps and perhaps even the re-insertion and later withdrawal again of the vitrectomy probe.

Of course, with each trip into and out of the eye, hazards associated with the insertion of an instrument into a patient's eye are multiplied. Each insertion risks leakage and the surgeon's own eyes need to adjust and re-adjust to the proper positioning of the tool to avoid injury. The surgeon's steadiness of instrument delivery must be repeated. This challenge may be increased given the ever-decreasing instrument size. For example, needles that traditionally may have been about 23 gauge may be about 25 or 27 gauge. This translates to reducing a needle diameter from just under about 0.5 mm (millimeters) to less than about 0.4 mm. Considering that a vitrectomy probe needle is likely to be of several millimeters in length and hollow, this increasingly thin gauge implement may be somewhat pliable. Other instruments dimensioned for working in the eye may likewise be somewhat pliable at small gauge size.

Further increasing the likelihood of injury due to added trips into the eye is the fact that another surgeon, nurse or other individual may also be involved with each trip, for example, to assist in taking away an instrument being withdrawn or selecting and handing over an instrument for insertion. This means that this other individual must also take care on each trip, for example, to hand over the proper instrument or to avoid unsteady contact with the surgeon.

SUMMARY

A tool for surgery (e.g., eye surgery) is provided which may be supported by a cannula at a surgical site on a patient. While examples provided herein may relate to eye surgery, it is to be understood that the tool can also be used for other surgery types (e.g., on other locations such at the abdomen) The tool includes a tubular guide for interfacing with the cannula. A first retractable implement is included that is extendable from a body of the tool and through the cannula to facilitate a first application in the eye during the surgery. A second retractable implement is also included that is extendable from the tool body and through the cannula to facilitate a second application in the eye during the surgery. Once more, the first retractable implement is retractable through the tubular guide during the extending of the second retractable implement.

DETAILED DESCRIPTION

In the following description, numerous details are set forth to provide an understanding of the present disclosure. However, it will be understood by those skilled in the art that the embodiments described may be practiced without these particular details. Further, numerous variations or modifications may be employed which remain contemplated by the embodiments as specifically described.

Embodiments are described with reference to certain types of surgical implement procedures. In particular, a vitrectomy probe and different forceps are highlighted in various figures. However, tools and techniques detailed herein may involve the use of a wide variety of different surgical implements that further eye surgery, whether or not such implements are specifically referenced herein. That is, the embodiments herein are not meant to be limited to these implements or others noted such as a backflush, a soft tip cannula, scissors, laser, scraper, light or a diathermy tool.

Further, while a vitrectomy and forceps procedure is largely discussed herein, embodiments of a multi-implement probe or device as detailed herein may be utilized to address retinal detachments, macular pucker, macular holes, vitreous floaters, diabetic retinopathy or a variety of other eye conditions. Indeed, so long as a surgical device is available that supports multiple implement types to minimize the number of trips into a patient's eye during a surgical procedure, appreciable benefit may be realized.

Figure 1:
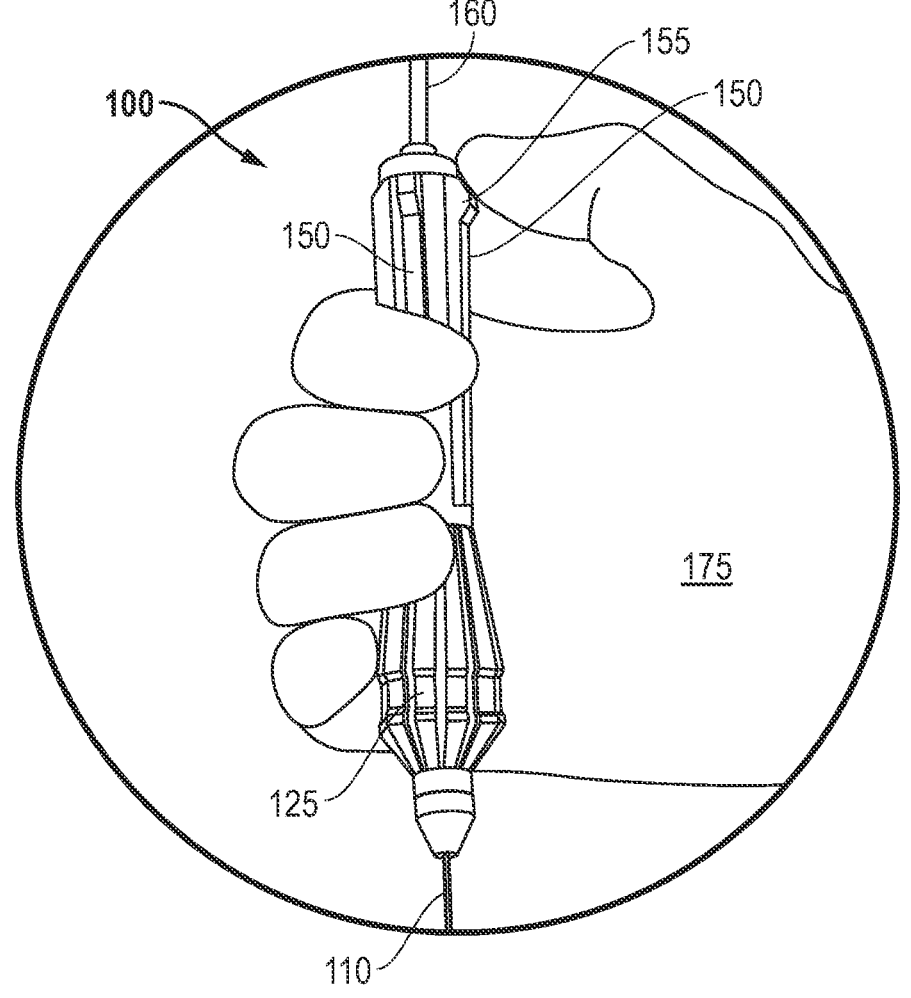
FIG. 1 is a side perspective view of an embodiment of a multi-implement eye surgical device.

Referring now to FIG. 1, a side perspective view of an embodiment of a multi-implement eye surgical device 100 is shown. Specifically, the device 100 is shown manually held in a gloved hand 175 of a surgeon as would be common for any number of different eye surgical device applications. The difference with the embodiment illustrated is that the single device 100 may support a wide variety of different applications. Thus, over the course of a given eye surgery, the need to set aside the device 100 for another is minimized. This means that the number of new trips into an eye 550 with an incredibly sharp, thin implement, may also be kept to a minimum (see FIGS. 5A and 5B).

As illustrated, the surgeon's thumb is located at a depressor 155 of a given actuator 150. Thus, with added reference to FIG. 3, the surgeon may be selecting a given implement (e.g. 310) for a certain procedure as part of an eye surgery. In the embodiment shown, the device 100 includes a body 125 from which a tubular guide 110 emerges for receiving the selected implement 310.

Figures 5A, 5B:
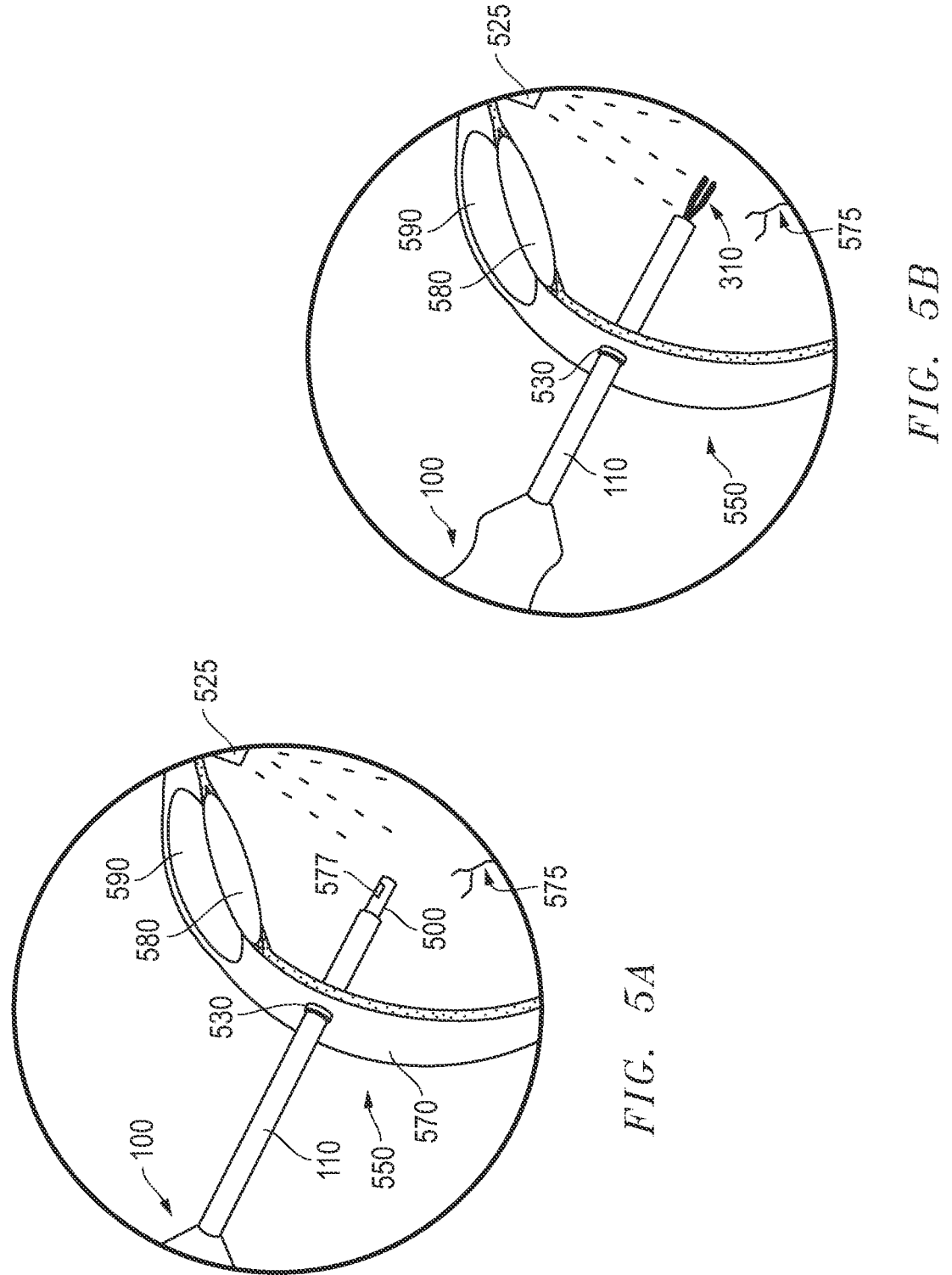
FIG. 5A is a perspective sectional view of a surgical procedure carried out by a first implement of the multi-implement eye surgical device of FIG. 1.
FIG. 5B is a perspective sectional view of the surgical procedure of FIG. 5A carried out by a second implement of the multi-implement eye surgical device of FIG. 1.

With added reference to FIGS. 5A and 5B, the tubular guide 110 may remain engaged with a cannula 530 throughout an eye surgery or at least between certain changeouts of implements (e.g. 500 and 310). Thus, as used herein, terminology such as "minimizing the number of trips into the eye" is not meant to infer that one implement is not withdrawn and exchanged for another that is advanced into the eye 550. Rather, this terminology is meant to highlight the fact that this implement exchange occurs with the tubular guide 110 remaining engaged with the cannula 530. Thus, from the perspective of the eye 550, a new engagement is not required. Therefore, from the vantage point of the eye 550 the exchange of implements may not constitute a "new trip" in the conventional sense given that the guide 110 has remained in place throughout.

Continuing with reference to FIG. 1, the embodiment of device 100 illustrated accommodates six different actuators 150 for six different implements. This is well illustrated at FIG. 4 which provides a good perspective of the device 100 and surgical options from the surgeon's perspective. Additionally, in the embodiment shown, backflush tubing 160 is illustrated which may support the use of backflush fluid that may be delivered through a dedicated backflush implement or even through the guide 110 in support of yet another surgical application. Thus, where the latter is the case, the device 100 effectively supports seven different surgical applications. Additionally, note that the tubing 160 may support a vitrectomy as detailed further herein.

Of course, the number of different application or implement types that may be accommodated by the device 100 is not set at any particular number. The number may range from two to more than seven. The minimizing of implement size over the years renders the six implement plus backflush embodiment illustrated to be a possible embodiment. In some embodiments, to keep the body 125 of sufficiently low profile for the surgeon, the device 100 may be intentionally limited to only a few implement options. For example, with a vitrectomy based surgical plan in place, the device 100 selected may include a vitrectomy probe implement plus one or two (or other numbers of) other implement types most likely to be of need according to the surgical plan.

It is of note that utilizing a device 100 with multiple implement options, not only reduces trips into the eye, potentially down to a single trip but also supplies other advantages of singularity. For example, a single device 100 means that there is a single manufacturing, single packaging, single sterilizing and single storage for multiple different implements. Thus, less waste and greater efficiencies are realized in a variety of different areas.

Figure 2:
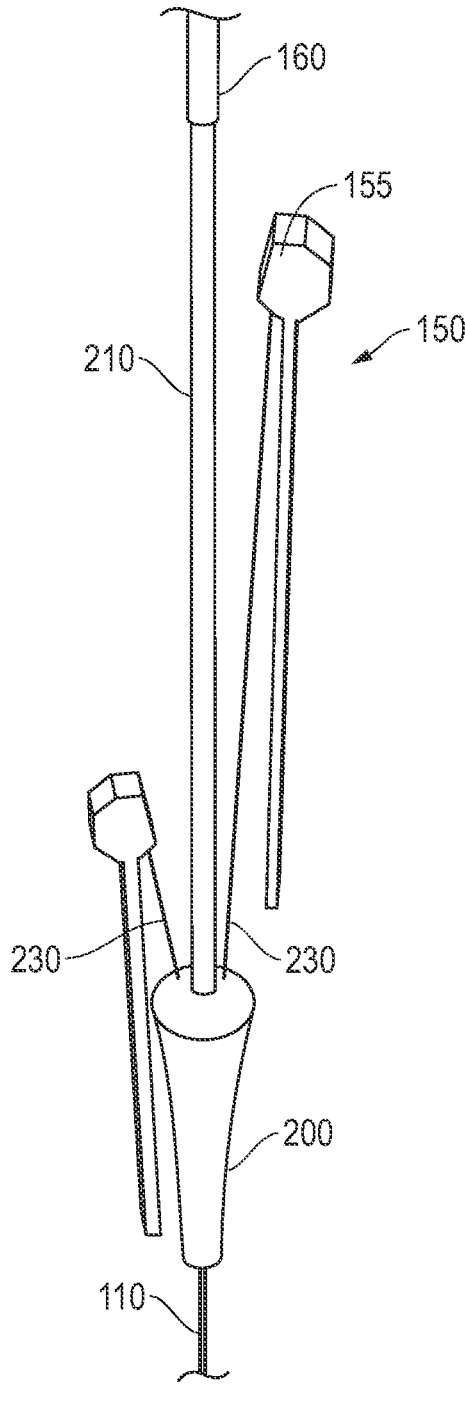
FIG. 2 is an exploded view of select internal architecture of the multi-implement eye surgical device of FIG. 1.

Referring now to FIG. 2, an exploded perspective view of select internal architecture of the multi-implement eye surgical device 100 of FIG. 1 is shown. Specifically, two implement actuators 150 are shown with depressors 155 as described above. The actuators 150 are visibly guided along an external side of the device body 125. In one embodiment, the external visibility is taken advantage of with the depressors 155 and actuators 150 being color-coded as indicative of the implement type. For example, a yellow actuator 150 may indicate association with a vitrectomy probe implement and a blue actuator 150 may indicate association with a forceps implement.

Figure 3:
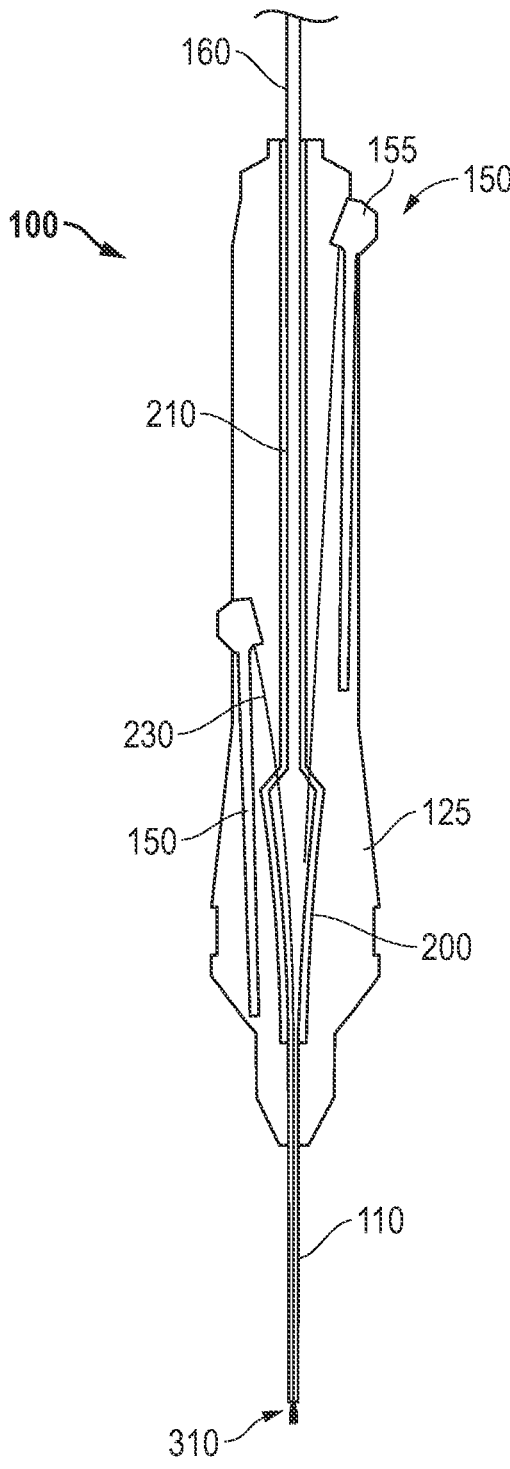
FIG. 3 is a side cross-sectional view of the select internal architecture of FIG. 2 within a body of the multi-implement eye surgical device of FIG. 1.

Not apparent in FIG. 1 is the driving mandrel 230 coupled to each actuator 150 for advancing the selected implement. With added reference to the cross-sectional view of FIG. 3, the driving mandrel 230 may be thought of as an extension of any given implement. For example, forceps 310 are shown as the implement selected in FIG. 3 by way of depressing the associated actuator 150 and driving mandrel 230 being depressed (as also shown in FIG. 2). The surgeon may even single-handedly, with but one finger, adequately drive this actuation. In the view of FIG. 3, it is apparent that the forceps implement is made up of the forceps 310 and the associated driving mandrel 230.

Continuing with reference to FIGS. 2 and 3, the driving mandrels 230 are guided through a center cap 200. It is the center cap 200 that plays the mechanical role in governing the advancement of one implement and the coordinated retraction of another. Additionally, internal tubing 210, coupled to the backflush tubing 160, is routed through the cap 200 to supply application fluid through the guide 110 for a surgical procedure when desired by the surgeon. Of course, where the application is a vitrectomy, the tubing 160, 210 may facilitate uptake of vitreous humor. Further, internal architecture of the device 100 may include substantially more features to drive reciprocation of a cutter (e.g., through an internal electrical or pneumatic drive that may use additional tubings (e.g., air supply tubing)/supply lines (e.g., electrical supply line) to the device 100 for operation of the drive).

With specific reference to FIG. 3, the selected implement 310 is a particular forceps that emerges from within the center cap 200. Notice that the center cap 200 is of a profile with a volume sufficient for accommodating several implements at the same time such as those illustrated at FIG. 4. Modern eye surgery implements, particularly the mandrel portion 230, may be 25 or 27 gauge (or other gauges), and well suited for such positioning. At the same time, however, the cap 200 also tapers at the lower end to the point that multiple implements may not, in some embodiments, occupy the exit from the cap 200 at the same time. Along these lines, when the surgeon selects an implement at the depressor 155, an automatic release may be triggered for the withdrawal of any implement that might already be within the tubular guide 110. Thus, a previously extended implement might recede to within the cap 200 before the newly selected implement reaches the guide 110. In this way, multiple implements becoming stuck within the guide 110 may be avoided. Once more, upon extension of the newly selected implement, a conventional automatic lock may be triggered within the cap 200 for stabilizing the implement for a surgical procedure. As suggested, this lock may be maintained until another selection with a depressor 155 is made by the surgeon.

Figure 4:
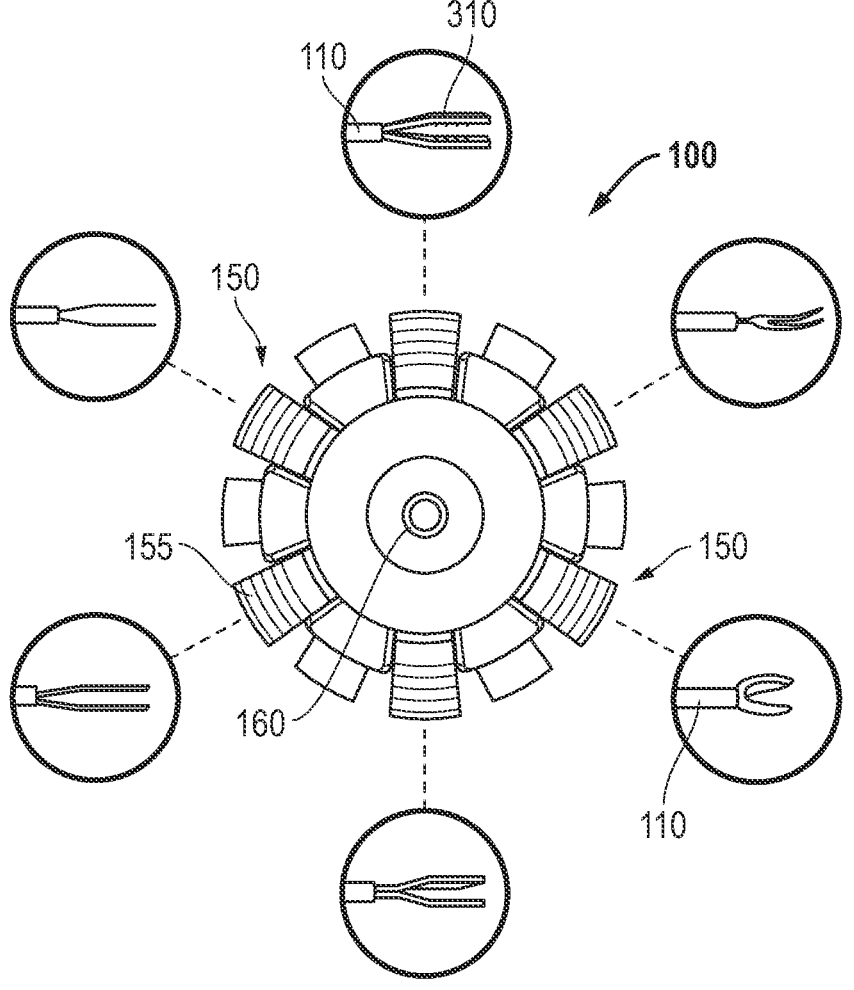
FIG. 4 is a top schematic view of the multi-implement eye surgical device from the perspective of a surgeon presented with multi-implement options.

Referring now to FIG. 4, a top schematic view of the multi-implement eye surgical device 100 is illustrated from the perspective of a surgeon utilizing the device 100. For example, by merely looking at the top of the device 100, the surgeon may be presented with a host of different implement options. In the illustration, six different implements are illustrated in an exploded manner (e.g. 310). However, as indicated above, the surgeon may actually be provided distinctive notice of the implement options through color-coding of the different sliders or actuators 150. The surgeon may select the depressor 155 accordingly. Of course, color-coding is not required. The actuators 150 or other adjacent device features may be labeled or some other form of indicator may be utilized.

Continuing with reference to FIG. 4, recall that the particular multi-implement device 100 illustrated also includes additional application support by way of backflush tubing 160 that may support a backflush application run centrally through the device 100 and out the guide 110 (see FIG. 3). Further, in the embodiment shown, the implements are differently sized jaws or forceps tools 310. However, in addition to forceps 310 and backflush tubing 160, the implement options may include, scissors, a laser, a scraper, light, a soft tip cannula, a diathermy tool or even a vitrectomy probe 500 (see FIG. 5A).

Referring now to FIG. 5A, a perspective sectional view is shown of a surgical procedure carried out by a first implement 500 of the multi-implement eye surgical device 100 of FIG. 1. In this embodiment, the surgeon's single hand 175 of FIG. 1 has manually selected an actuator 150 associated with a vitrectomy probe 500. A preplaced cannula 530 is positioned in an offset manner at the sclera 570. In this way, the more delicate cornea 590 and lens 580 may be avoided.

During the vitrectomy, the probe implement 500 is advanced through the guide 110 that has been pre-placed through the cannula 530. In the embodiment shown, the guide is entirely through the cannula 530, reaching into the interior of the eye 550. However, in other embodiments, the guide 110 may serve to provide structural support for the implements and interface the cannula 530 in a stabilizing manner, avoiding traversal into the eye 550. In the embodiment shown, the vitrectomy probe implement 500 is directed toward a region 575 illuminated by a light instrument 525 where vitreous humor is to be removed. Specifically, a suction is applied through the backflush 160 and interior 210 tubing and a port 577 is used for the uptake of the vitreous humor or other substances (see also FIG. 2).

For sake of illustration, FIGS. 5A and 5B present a circumstance in which the surgeon may want to switch between implements being utilized. For example, in the procedure illustrated, a hemorrhage or other damaged tissue may present for which the surgeon might prefer to utilize a forceps implement 310 for a period before further uptake with the probe 500. Thus, with specific reference to FIG. 5B, the surgeon simply selecting another implement by depressing the appropriate actuator 150 to switch out a vitrectomy probe 500 for forceps 310 has occurred (see also FIG. 1).

Notice that the described implement switch out does not require any repositioning of the device 100. Indeed, as would commonly be the case, the second implement 310 is also directed at the same region 575 as the first 500. That is, the surgeon has simply decided to address a given issue with a different implement. No re-inserting the device 100 through the cannula 530 is required. Thus, even after briefly looking at the back of the device 100 to select a new implement 310, regaining visualization of the region 575 may also be easier for the surgeon, given the fact that the device 100 is already pointing to the region 575. The avoidance of an extra trip into the eye 550 is also avoided when the surgeon similarly decides to resume a vitrectomy application for uptake of vitreous humor and tissue broken up or otherwise addressed by the forceps 310.

In the embodiment of FIGS. 5A and 5B, the guide 110 is shown through the cannula 530. As noted above, the guide 110 may instead serve to provide structural support and stably rest in interface with the cannula 530 to support the procedure. However, in yet another embodiment, the end of the guide 110 may be equipped with a knife and take on the architecture of a cannula. Thus, the separate use of a cannula 530 may be avoided with the guide 110 behaving as a combination support and cannula device, supporting the delivery of any number of implements as detailed hereinabove.

Figure 6:
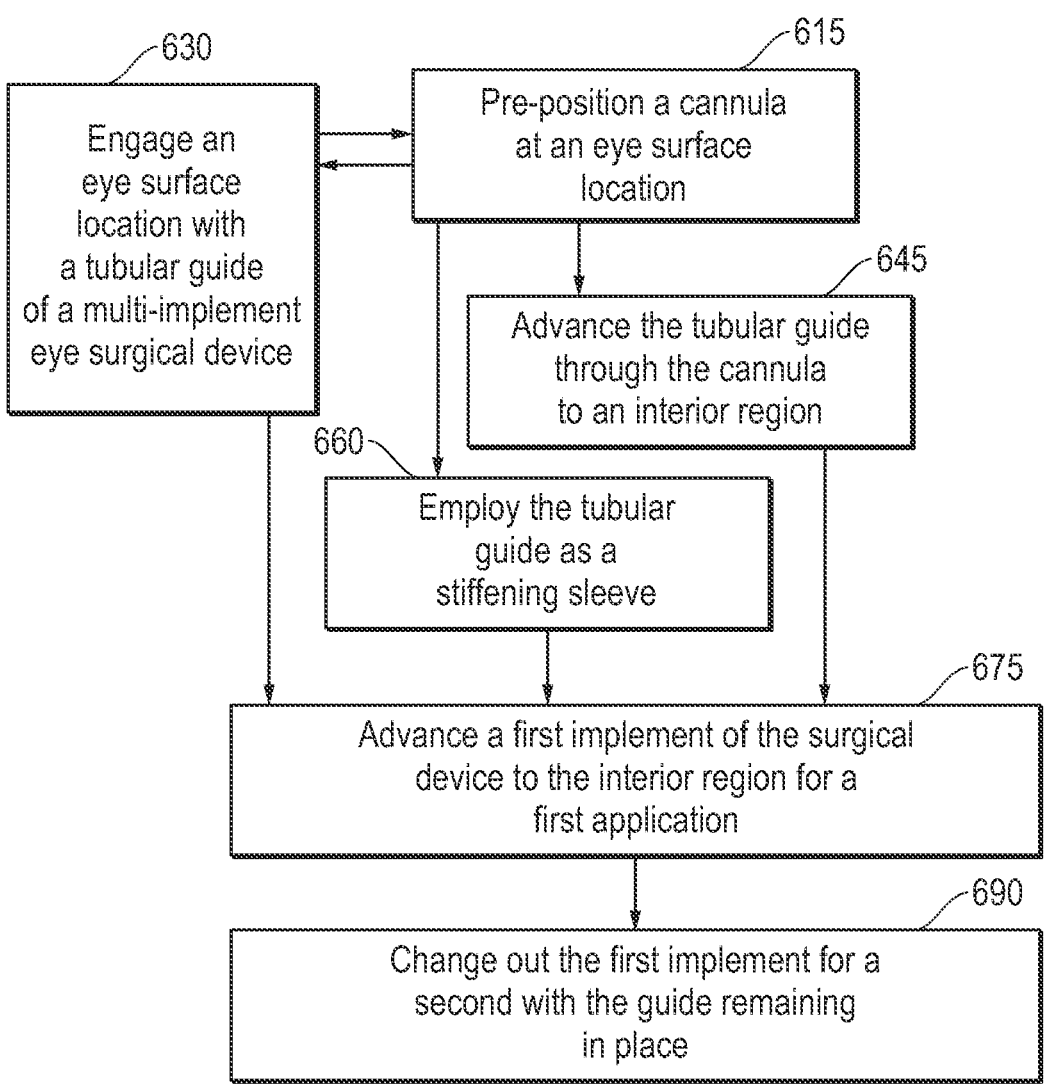
FIG. 6 is a flow-chart summarizing an embodiment of performing a minimally invasive eye surgery with a multi-implement eye surgical device.

Referring now to FIG. 6, a flow-chart is shown summarizing an embodiment of performing a minimally invasive eye surgery with a multi-implement eye surgical device. As indicated at 615 and 630, a cannula may or may not be preplaced at a surface location of an eye to help facilitate reception of a tubular guide of the device. Once more, as indicated at 645 and 660, the tubular guide may traverse to an interior region of the eye or it may serve more of a structural support. Regardless, the device supports the further advancement of a surgical implement through the guide and to the interior region for a surgical procedure (see 675). Furthermore, the first implement may be changed out for a second implement while the guide remains in place as indicated at 690. Indeed, this type of changeout may be repeated with the same device and a host of different implements without ever necessitating disengagement of the guide from the eye. Thus, hazards associated with device re-engagement every time a new trip with a new implement takes place may be avoided.

The preceding description has been presented with reference to the provided embodiments. However, other embodiments and/or features of the embodiments disclosed but not detailed hereinabove may be employed. Furthermore, persons skilled in the art and technology to which these embodiments pertain will appreciate that still other alterations and changes in the described structures and methods of operation may be practiced without meaningfully departing from the principle and scope of these embodiments. Additionally, the foregoing description should not be read as pertaining only to the precise structures described and shown in the accompanying drawings, but rather should be read as consistent with and as support for the following claims, which are to have their fullest and fairest scope.

The invention claimed is:

1. A multi-implement device for surgery at a surgical site on a patient, the device comprising:

a tubular guide;

a first retractable surgical implement to extend from a body of the device and through the tubular guide to facilitate a first application during the surgery; and a second retractable surgical implement to extend from the body and through the tubular guide to facilitate a second application during the surgery, the first retractable surgical implement retracted through the tubular guide during the extending of the second retractable surgical implement;

wherein the device comprises a proximal end and a distal end;

wherein the tubular guide extends from the distal end;

wherein the first retractable surgical implement comprises a first driving mandrel coupled to a first actuator specific to the first retractable surgical implement;

wherein the second retractable surgical implement comprises a second driving mandrel coupled to a second actuator specific to the second retractable surgical implement;

wherein the first and second actuator are accessible by a finger of a user and are configured to be driven linearly toward the distal end upon being depressed by the finger toward the distal end for deployment of a corresponding first or second retractable surgical implement; and wherein depression of the first or second actuator by the finger toward the distal end results in a corresponding release of the other of the first or second actuator and a subsequent linear travel of the other of the first or second retractable surgical implement toward the proximal end of the device to retract the corresponding first or second retractable surgical implement.

2. The multi-implement device of claim 1 wherein the retractable surgical implements are selected from a group consisting of a vitrectomy probe, forceps, a backflush device, scissors, a soft tip cannula, a laser tool, a scraper, a light, and a diathermy tool.

3. The multi-implement device of claim 1 further comprising one of backflush, a soft tip cannula and vitrectomy tubing coupled to the body at an end opposite an end from which the implements extend.

4. The multi-implement device of claim 1, wherein the tubular guide is configured to interface with a cannula at the surgical site.

5. The multi-implement device of claim 1, wherein the first and second actuators are provided with different visibly distinctive indicators for a surgeon to differentiate the implements.

6. The multi-implement device of claim 5 wherein the visibly distinctive indicators are different colors.

7. The multi-implement device of claim 1, further comprising a third retractable surgical implement to extend from the body and through the tubular guide to facilitate a third application during the surgery, the first or second retractable surgical implements retracted through the tubular guide during the extending of the third retractable surgical implement.

8. The multi-implement device of claim 7, wherein the third retractable surgical implement comprises a third driving mandrel coupled to a third actuator specific to the third retractable surgical implement;

wherein the third actuator is accessible by the finger of the user and is configured to be driven linearly toward the distal end upon being depressed by the finger toward the distal end for deployment of the third retractable surgical implement; and wherein depression of the third actuator by the finger toward the distal end results in a corresponding release of any deployed actuator of the first and second actuator and a subsequent linear travel of the corresponding deployed first or second retractable surgical implement toward the proximal end of the device to retract the corresponding first or second retractable surgical implement.

* * * * *